United States Patent [19]

Bennett

[11] Patent Number: Plant 5,437

[45] Date of Patent: Apr. 16, 1985

[54] MINIATURE ROSE PLANT

[76] Inventor: Cecilia L. D. Bennett, 489 Minot Ave., Chula Vista, Calif. 92010

[21] Appl. No.: 525,497

[22] Filed: Aug. 22, 1983

[51] Int. Cl.[3] ..... A01H 5/00

[52] U.S. Cl. ..... Plt./9

[58] Field of Search ..... Plt./9

*Primary Examiner*—Robert E. Bagwill

[57] ABSTRACT

The subject of the present disclosure is a new and distinct variety of miniature rose plant, named 'My Delight', which is characterized by its blooms of pale Azalea Pink with slightly deeper inner petals and exceptionally good form.

1 Drawing Figure

The present invention relates to a new and distinct variety of a hardy, dwarf, bush plant of the miniature class; the variety being primarily characterized as a light pink.

The variety is further characterized by:

Long stemmed blooms of exceptionally good 'hybrid tea-type' form, borne primarily one to a stem but on occasion in sprays of 3 to 5 or more. The blooms are held very erect and well above the foliage.

It has a slight fragrance.

The plant ranges in height from 12 to 18 inches. The canes are slender but held very erect with moderate branching and medium foliage covering. The plant is a heavy bloomer that does well either outdoors or in the green house.

The plant has good growth habits, well shaped and attractive, with medium green leaflets of average size for a miniature variety.

The seed parent was Futura (U.S. Plant Pat. No. 3,569), and the pollen parent was Avandel (U.S. Plant Pat. No. 4,366).

Subsequent to the origination of the variety, I have successfully reproduced it at TINY PETALS NURSEY located at aforesaid retaining the distinguishing characteristics through succeeding propagations by cuttings.

The descriptive matter which follows pertains to roses grown and color values observed in plants and newly opened blooms in the month of August. The plants were grown outdoors in Chula Vista, Calif., and are believed to be accurate standards for this cultivar in similar conditions of soil and climate elsewhere.

The color photograph illustrates the variety.

Referring now specifically to the new and distinct variety of miniature rose plant named 'My Delight', the following is a detailed description thereof in outline; all major color plate identifications being by reference to the British Colour Council Horticultural Colour Chart, except where common terms of color definition are employed.

Type: Hardy, dwarf, green house or outdoor, exhibition quality or garden decorative potted plant.

Class: Miniature.

Variety name: My Delight.

Flowers borne: Usually one to a stem, but occasionally in sprays of 3 to 5 or more on erect stems with the foliage well below the blooms.

Quantity of bloom: Heavy both outdoors or green house grown.

Bud:

*Peduncle.*—Medium to long (30 to 45 mm); average diameter and sturdy; near Pod Green (061 to 061/1 page 120) with occasional light tinting of bronze.

*Hairs.*—Extremely small and numerous; located over the entire surface of the peduncle, calyx and sepals.

*Calyx.*—Color near Pod Green (061 to 061/1 page 120).

*Opening.*—Opens well in all weather.

Bloom: Size when fully opened - Average for a miniature variety (35 to 45 mm).

*Petalage.*—Double — Averaging about 20 to 30 petals, arranged regularly, plus petaloids (6 to 12 or more).

*Form.*—Urn-shaped to ovoid as the bloom progresses. The petals remain at first somewhat tightly cupped with the tips and/or margins refexed outward, becoming at maturity more loosely cupped. As the bloom opens, the petals (starting with the outermost and progressing to the innermost) begin to reflex at the margins, rolling under from the apex of the petals on both sides. This 'quilling' may not always occur, depending on the weather and soil conditions at the time; or the effect may be more of a soft curling under of the petals.

Petals: Fairly thick with good substance, though deceptively delicate looking to the eye; under surface has a matte finish, while the upper surface has a slight 'pearl-like' sheen.

*Shape.*—Outer petals are of a very broad obovate form with an extremely slight peak at the apex. The intermediate petals are narrower than the outer petals with a more noticeable peak at the apex. The inner petals are more like broad lanceolates, and the petaloids are like small lanceolate with occasional irregularities in shape.

Color (newly opened flowers from plants grown outdoors, August 1983, Chula Vista, Calif.):

*Outside petals.*—Upper surface — Ranging from near Azalea Pink (618/3 to 618/2 page 74) to near Rose Pink (427/3 to 427/2 page 126) from the margin to approximately two thirds of the petal; a small area at lower portion of petal is white with a tip near Naples Yellow (403/2 to 403/1 Page 121).

*Under surface.*—Ranging from near Azalea Pink (618/3 page 74) to near Rose Pink (427/3 page 126) with a small area at the base of white and a tip near Naples Yellow (403/3 page 121).

*Intermediate and inner petals.*—Upper surface — Ranging from near Azalea Pink (618/2 to 618/1 page 74) to near Rose Pink (427/1 to 427 page 126) from the margin to approximately two thirds of the petal; a small area at the lower portion of the petal is white with a tip near Naples Yellow (403/2 to 403/1 page 121).

*Under surface.*—Ranging from near Azalea Pink (618/2 to 618/3 page 74) to near Rose Pink (427/2 to 427/3 page 126) with a small area at the base of white and a tip near Naples Yellow (403/3 page 121).

*General color effect.*—Newly opened flowers — Very soft shades of pink with slightly deeper pastel pink at the center of the bloom. Three days open — No fading; more of the deeper pink petals visible. Five to seven days — Slight fading of the outer petals and obvious quilling of almost all of petals. Spent petals drop off cleanly.

*Flower longevity.*—(August 1983) Plant in pot 4 to 7 days from bud with sepals down to fully opened bloom. Holding at fully open with only slight fading of the outermost petals for an additional 3 to 4 days before bloom begins to drop petals. Cut blooms at livingroom temperature 4 to 5 days or longer.

Reproductive organs:

*Stamens.*—A generous amount arranged uniformly around the pistil.

*Filaments.*—Varying in length, pale yellow in color.

*Pollen.*—Abundant.

*Pistil.*—Long, abundant and spreading; pale yellow at the base and reddish near the top.

*Styles.*—Long and uniform in length; pale yellow to reddish in color.

*Ovaries.*—All encased in the calyx.

*Hips.*—Some.

*Seed.*—Few or none.

*Sepals.*—Permanent; spear-shaped; open as the bloom opens; recurves against the peduncle as the flower matures.

Foliage:

*Leaves.*—Five to seven leaflets on the average; medium size for a miniature rose plant.

*Leaflets.*—Broad ovate-shaped.

*Margin.*—Very serrated with occasional tinting of bronze, especially noticeable on the newer foliage.

*Color.*—Ranging from near Scheeles Green (860/3 to 860 page 175) to near Spinach Green (0960/3 to 0960 page 187) with occasional bronzing of the margins. The upper surfaces have a satiny finish, and the under surfaces have a matte finish of a slightly lighter shade than the upper surfaces.

*Rachis.*—Medium strength; upper surface is grooved with some small hairs at the edge. Under surface contains only a few small hairs or prickles and very rarely a small thorn or two.

*Stipules.*—Varying in length from medium to very small; average width; tapering auricles angled outward at about 45 degrees.

Growth:

Habit.—Dwarf; moderate foliage covering; average height for a miniature rose plant.

*Growth.*—Vigorous.

*Canes.*—Slender; sturdy; held very erect.

*Main stems.*—Color — Ranging from near Scheeles Green (860 page 175) to near Spinach Green (0960/3 page 187) with occasional bronzing, especially noticeable on the newer stems.

Thorns.—Averaging 3 to 5 small thorns per 10 cm on the main stems and branches. Very small and slender; straight or hooked slightly downward.

*Branches.*—Color — Same as the main stems.

The miniature rose plant and its flowers as herein described may vary in slight detail due to climate, soil and cultural conditions under which the variety may be grown; the present description being of the variety as grown at Chula Vista, Calif.

The following is claimed:

1. A new and distinct variety of miniature rose plant named 'My Delight' of hardy, dwarf, vigorous growth, attractive in appearance, substantially as illustrated and described, characterized by its blooms of pale pink with slightly deeper pink inner petals and exhibition form, easy to propagate from cuttings, with flowers borne usually one to a stem, but occasionally in sprays of 3 to 5 or more.

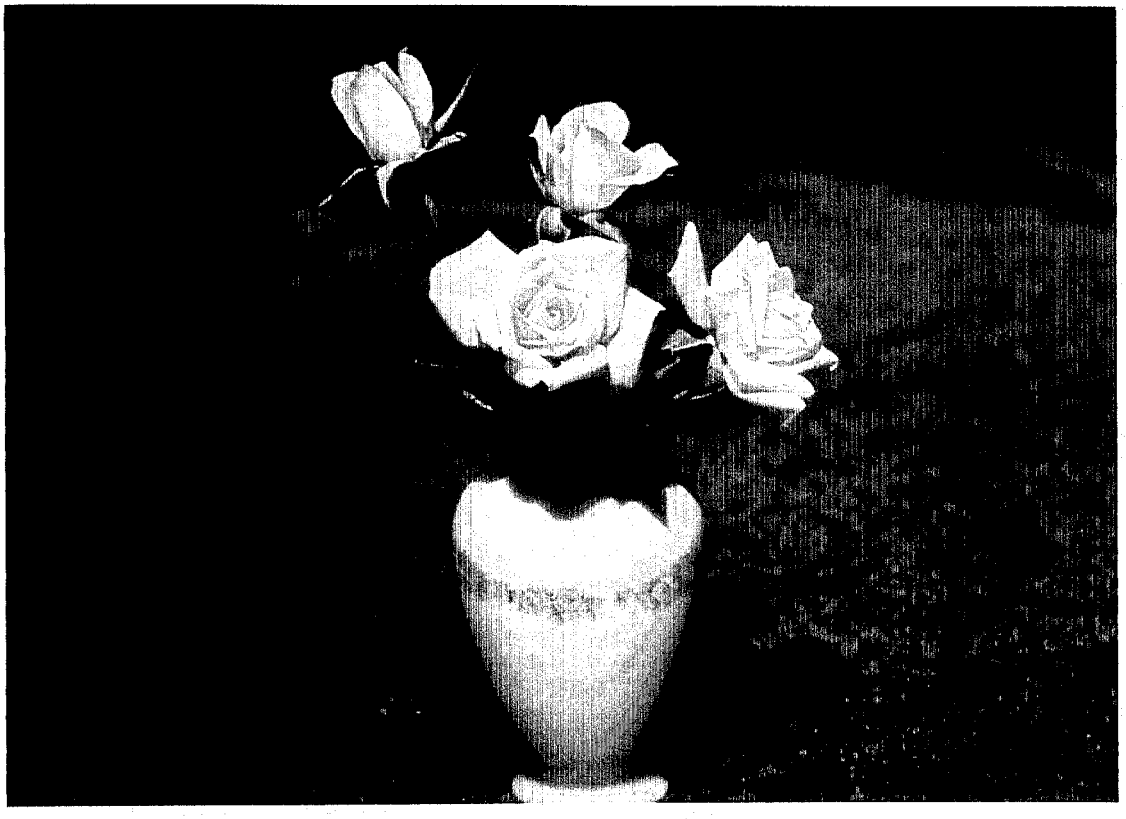

* * * * *